US008461377B2

(12) United States Patent
Hassan et al.

(10) Patent No.: US 8,461,377 B2
(45) Date of Patent: Jun. 11, 2013

(54) HIGH SHEAR PROCESS FOR ASPIRIN PRODUCTION

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 275 days.

(21) Appl. No.: 12/144,327

(22) Filed: Jun. 23, 2008

(65) Prior Publication Data

US 2009/0005592 A1 Jan. 1, 2009

Related U.S. Application Data

(60) Provisional application No. 60/946,500, filed on Jun. 27, 2007.

(51) Int. Cl.
*C07C 67/08* (2006.01)

(52) U.S. Cl.
USPC ........................................................ 560/254

(58) Field of Classification Search
CPC ................................................... C07C 69/157
See application file for complete search history.

(56) References Cited

U.S. PATENT DOCUMENTS

| | | | |
|---|---|---|---|
| 373,187 A * | 11/1887 | Edmunds | 172/693 |
| 644,077 A | 2/1900 | Hoffman | |
| 671,769 A | 4/1901 | Leonhard | |
| 2,987,539 A | 6/1961 | Stroesser et al. | |
| 3,235,583 A | 2/1966 | Edmunds et al. | |
| 3,887,167 A | 6/1975 | Irwin | |
| 4,107,792 A * | 8/1978 | Durr | 366/302 |
| 5,279,463 A * | 1/1994 | Holl | 241/1 |
| 5,538,191 A | 7/1996 | Holl | |
| 5,877,350 A | 3/1999 | Langer et al. | |
| 6,278,014 B1 | 8/2001 | Handal-Vega et al. | |
| 6,368,366 B1 | 4/2002 | Langer et al. | |
| 6,368,367 B1 | 4/2002 | Langer et al. | |
| 6,383,237 B1 | 5/2002 | Langer et al. | |
| 6,530,964 B2 | 3/2003 | Langer et al. | |
| 6,742,774 B2 | 6/2004 | Holl | |
| 2003/0043690 A1 | 3/2003 | Holl | |
| 2004/0052158 A1 | 3/2004 | Holl | |
| 2004/0191667 A1 | 9/2004 | Kurokawa et al. | |
| 2005/0033069 A1 | 2/2005 | Holl et al. | |

FOREIGN PATENT DOCUMENTS

WO 02064708 A2 8/2002

OTHER PUBLICATIONS

International Search Report, International Application No. PCT/US2008/067995, dated Dec. 31, 2008.
IKA-Rotor-Stator Generators—2003 Processing Ctalog (38 pgs.).
Gogate, et al. "Cavitation: A technology on the horizon," Current Science 91, No. 1, Jul. 2006, pp. 35-46 (12 pgs.).
Office Action dated Jun. 25, 2009 for U.S. Appl. No. 12/142,447 (10 pgs.).
Office Action dated Jan. 7, 2010 for U.S. Appl. No. 12/142,447 (6 pgs.).
Office Action dated May 13, 2010 for U.S. Appl. No. 12/142,447 (5 pgs.).
Office Action dated Feb. 4, 2010 for U.S. Appl. No. 12/492,721 (5 pgs.).
Office Action dated Feb. 18, 2010 for U.S. Appl. No. 12/635,433 (6 pgs.).
Office Action dated Feb. 18, 2010 for U.S. Appl. No. 12/635,454 (6 pgs.).
Office Action dated May 14, 2010 for U.S. Appl. No. 12/137,441 (15 pgs.).
Office Action dated Feb. 19, 2010 for U.S. Appl. No. 12/144,459 (10 pgs.).
Office Action dated Sep. 2, 2009 for U.S. Appl. No. 12/142,433 (11 pgs.).
Office Action dated Jan. 29, 2010 for U.S. Appl. No. 12/142,433 (8 pgs.).
Office Action dated May 24, 2011 for U.S. Appl. No. 12/142,433 (10 pgs.).
Office Action dated Apr. 30, 2010 for U.S. Appl. No. 12/141,191 (12 pgs.).
Office Action dated Oct. 27, 2009 for U.S. Appl. No. 12/142,120 (15 pgs.).
Office Action dated May 5, 2010 for U.S. Appl. No. 12/571,537 (12 pgs.).
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
Office Action dated Jun. 2, 2011 for U.S. Appl. No. 12/427,286 (12 pgs.).

(Continued)

*Primary Examiner* — Paul A Zucker
(74) *Attorney, Agent, or Firm* — Porter Hedges LLP; Timothy S. Westby

(57) ABSTRACT

Use of a high shear mechanical device in a process for production of acetyl salicylic acid, by contacting acetic anhydride with salicylic acid in a high shear device. The disclosed process makes possible a decrease in mass transfer limitations, thereby enhancing production of acetyl salicylic acid. A system for production of acetyl salicylic acid is also provided in which a reactor is configured to receive the output from a high shear device, which is configured to receive, via one or more inlets, acetic anhydride, and salicylic acid and generate a fine dispersion or emulsion of reactants.

14 Claims, 2 Drawing Sheets

OTHER PUBLICATIONS

Office Action dated Jun. 3, 2011 for U.S. Appl. No. 12/568,280 (16 pgs.).

IKA, "Introduction to IKA's Three Stage Dispax Reactor," Retrieved from <http://www.ikausa.com/pdfs/process/dr%202000-Homogenizing-Dispersing-Suspending-Emulsifying.pdf> on Aug. 22, 2012 (12 pgs.).

IKA-DRS Reactors website http://www.ikausa.com/dr.him, on Sep. 8, 2010 (2 pgs.).

* cited by examiner

HIGH SHEAR PROCESS FOR ASPIRIN PRODUCTION

CROSS-REFERENCE TO RELATED APPLICATIONS

This application claims the benefit under 35 U.S.C. §119(e) of U.S. Provisional Patent Application No. 60/946,500 filed Jun. 27, 2007, the disclosure of which is hereby incorporated herein by reference.

STATEMENT REGARDING FEDERALLY SPONSORED RESEARCH OR DEVELOPMENT

Not Applicable.

BACKGROUND OF THE INVENTION

1. Technical Field

The present disclosure relates generally to the production of acetyl salicylic acid, more commonly known as aspirin, and more particularly to apparatus and methods for converting acetic anhydride and salicylic acid to aspirin. More specifically, the disclosure relates to the reduction of mass transfer limitations in the esterification reaction to produce aspirin.

2. Background of the Invention

Acetyl salicylic acid, commonly known as aspirin, is among the most successful pharmaceutical products in the world. Medically, aspirin has been used as an analgesic and fever reducing agent, applications that continue to be recognized today. Recently research has shown that aspirin reduces the likelihood of strokes, heart attacks, and complications due to these conditions when administered after a cardiovascular incident. Furthermore, a low dose daily aspirin regimen has been demonstrated to reduce the likelihood of subsequent heart attack. As aspirin use includes minimal side effects and/or complications, aspirin is the one of most widely used pharmaceutical agents in the world. Continuing research may demonstrate further applications, such that its therapeutic uses continue to increase.

Commercially, aspirin is synthesized using a two-step process. Phenol, generally extracted from coal tar, is treated with sodium base to generate sodium phenoxide. Sodium phenoxide is then reacted with carbon dioxide under high temperature and pressure to yield salicylate, which is acidified to obtain salicylic acid. This process is known as the Kolbe-Schmitt reaction. Salicylic acid is acetylated with acetic anhydride to produce aspirin and acetic acid as byproduct.

The original U.S. patent covering the compound acetyl salicylic acid is U.S. Pat. No. 644,077, issued Feb. 27, 1900, in the name of Felix Hoffman. The Hoffman patent describes that the compound exhibits therapeutic properties. In the disclosure, a single synthetic procedure for its manufacture is taught, comprising refluxing salicylic acid and acetic anhydride for approximately two hours at 150° C.

Described in U.S. Pat. No. 671,769 is a process for producing acetylsalicylic acid by substituting the acetyl group for the hydrogen of the hydroxyl group in salicylic acid and derivatives. The reaction is effected by the reciprocal action of salicylic acid and acetic anhydride in the presence of a condensing agent. The condensing agent disclosed is concentrated sulfuric acid.

U.S. Pat. No. 3,235,583 discloses a method of synthesizing acetyl salicylic acid without the use of strong agents. The process is asserted to provide products with high purity and near theoretical yields, without using extreme or multiple recrystallization steps. The disclosed process incorporates a mixture of salicylic acid and acetic anhydride at from 40° C. to 95° C., with an approximately 20% molar excess of acetic anhydride. The mixture is reacted in a closed vacuum-equipped vessel at the elevated temperature. The process continues maintaining the elevated temperature while reducing the internal pressure. The process maintains a partial vacuum within the range of about $1.5 \times 10^{-1}$ torr to $2.2 \times 10^{-1}$ torr. During the reaction, it is asserted that reducing the pressure gradually to within the range of from about $3.9 \times 10^{-2}$ torr to a minimum attainable pressure, while maintaining the elevated temperature and reduced pressure at the lower range for about 1 to 3 hours, and thereafter recovering crystalline acetyl salicylic acid from the reaction vessel. In this process, special reaction vessels are needed, pressure within the vessel must be actively controlled, and a number of hours are needed for reaction completion.

U.S. Pat. No. 3,373,187 describes a method of synthesizing aspirin by the reaction of acetic anhydride and salicylic acid using a catalytic metal salt such as $Mg(OH)_2$. In the disclosure, reaction times of about 2 to 11 hours are presented. Typical catalytic salts mentioned as suitable for the process are magnesium hydroxide, nickel hydroxide, calcium nitrate, cobalt nitrate, and magnesium acetate. Furthermore, the concentration for the catalyst is described as between 25 ppm and 500 ppm. Large quantities of the preferred $Mg(OH)_2$ catalyst produce significant quantities of water and Mg acetate. These products cause undesirable decomposition of the aspirin product.

U.S. Pat. No. 6,278,014 describes a process wherein CaO and/or ZnO are used in the synthesis of acetyl salicylic acid. The patent discloses the addition of calcium oxide or zinc oxide to a reaction mixture comprising stoichiometric amounts of acetic anhydride and salicylic acid. The reaction is asserted to produce aspirin having less than 2% of free salicylic acid content. Furthermore, the use of CaO or ZnO in the process eliminates the need for additional organic solvents, or recrystallization. The catalyzed process yields a dense product. In certain instances, this product may be directly mixed with common excipients. Further, the acetyl salicylic acid and excipient mixture may be compressed into tablets upon synthesis. The process forms a significant quantity of Ca acetate and/or Zn acetate.

Accordingly, there is a need in the industry for improved methods of producing acetylsalicylic acid from acetic anhydride and salicylic acid, whereby production rates are increased, unwanted reactions are reduced, and milder reaction conditions, such as lower temperature, and pressure, are commercially feasible.

SUMMARY OF THE INVENTION

A high shear system and process for accelerating acetyl salicylic acid production is disclosed. The disclosed high shear method reduces mass transfer limitations, thereby improving reaction conditions in the reactor such as the reaction rate, temperature, pressure, contact time, and/or product yield. In accordance with certain embodiments of the present disclosure, a process is presented that makes possible an increase in the rate of a liquid phase process for the production of chloral from acetaldehyde by providing for more optimal time, temperature, and pressure conditions than are currently used.

In an embodiment described in the present disclosure, a process employs a high shear mechanical device to provide enhanced time, temperature, and pressure reaction conditions resulting in accelerated chemical reactions between multiphase reactants.

In an embodiment, the method comprises the use of a pressurized high shear device to provide for production of acetyl salicylic acid, with improved synthesis reaction properties.

These and other embodiments, features, and advantages will be apparent in the following detailed description and drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

Overview

Figure 1:
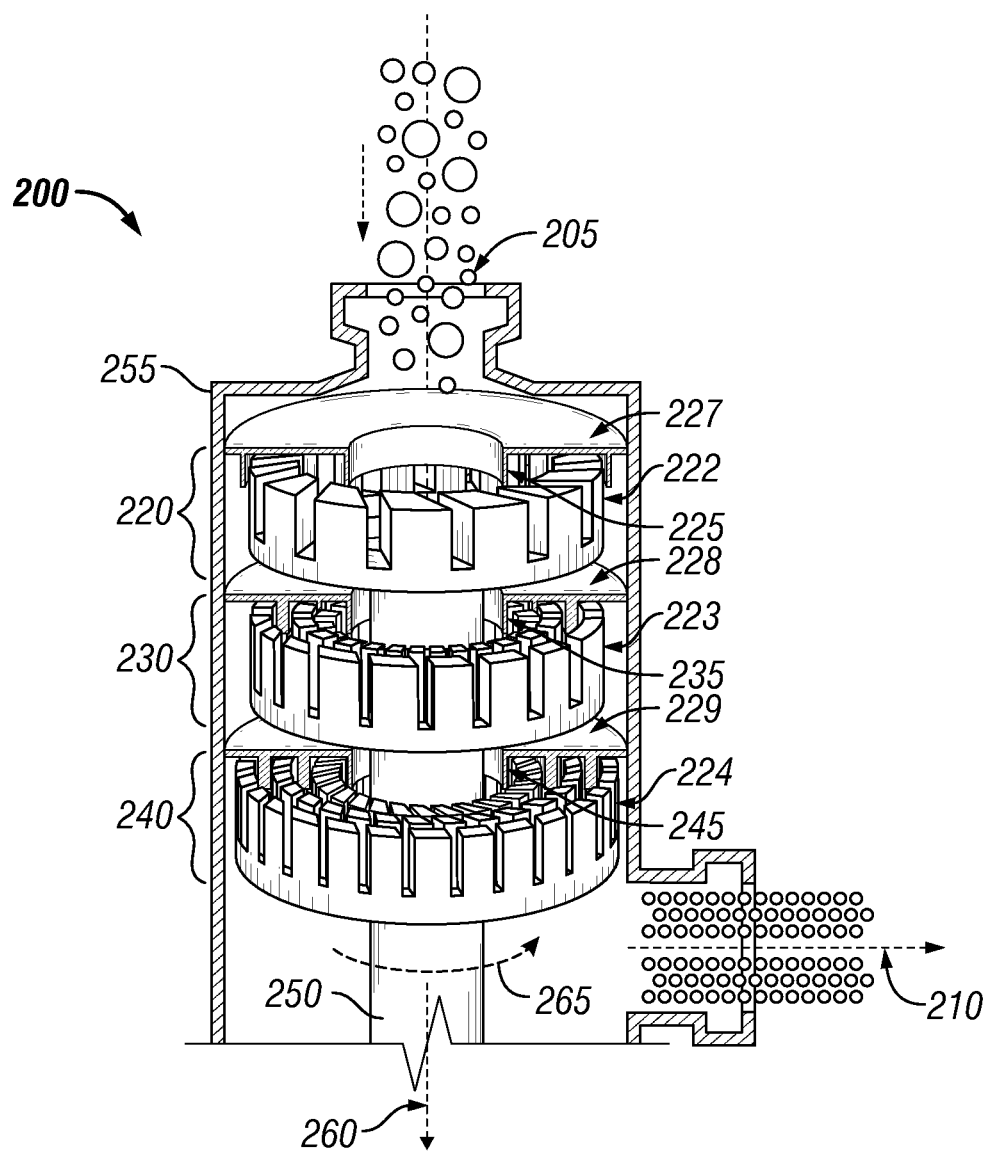
FIG. 1 is a cross-sectional diagram of a high shear device for the production of aspirin.

The present disclosure provides a system and method for the synthesis of acetyl salicylic acid comprising mixing acetic anhydride and salicylic acid with a high shear device. The synthesis of aspirin is classified as an esterification reaction, wherein the alcohol group from the salicylic acid reacts with an acid (acetyl anhydride) to yield the ester. The system and method disclosed herein for the production of aspirin from salicylic acid and acetic anhydride employs a high shear mechanical device to provide rapid contact and mixing of reactants in a controlled environment comprising the high shear reactor/mixer device.

A system and method employ a high shear mechanical device to provide rapid contact and mixing of chemical ingredients in a controlled environment in the reactor/mixer device. The high shear device reduces the mass transfer limitations on the reaction and thus increases the overall reaction rate.

Chemical reactions involving liquids, gases, and solids rely on the laws of kinetics that involve time, temperature, and pressure to define the rate of reactions. Where it is desirable to react two or more raw materials of different phases (e.g. solid and liquid; liquid and gas; solid, liquid and gas), one of the limiting factors controlling the rate of reaction is the contact time of the reactants. In the case of heterogeneously catalyzed reactions, there may be an additional rate limiting factor, namely, removing the reaction products from the surface of the catalyst to enable the catalyst to catalyze further reactants.

In conventional reactors, contact time for the reactants and/or catalyst is often controlled by mixing which provides contact between two or more reactants involved in a chemical reaction. A reactor assembly that comprises a high shear device makes possible decreased mass transfer limitations and thereby allows the reaction to more closely approach kinetic limitations. When reaction rates are accelerated, residence times may be decreased, thereby increasing obtainable throughput. Alternatively, where the current yield is acceptable, decreasing the required residence time allows for the use of smaller amounts of reactant, for example, acetic anhydride, organic diluent, acid catalyst, catalytic metal salt, zinc oxide, and/or calcium oxide, thus improving the process economics.

High Shear Device

High shear devices (HSD) such as high shear mixers and high shear mills, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid. The classes are distinguished based on delivered energy density. There are three classes of industrial mixers having sufficient energy density to consistently produce mixtures or emulsions with particle or bubble sizes in the range of 0 to 50 µm.

Homogenization valve systems are typically classified as high-energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and may yield average particle size range from about 0.01 µm to about 1 µm. At the other end of the spectrum are high shear mixer systems classified as low energy devices. These systems usually have paddles or fluid rotors that turn at high speed in a reservoir of fluid to be processed, which in many of the more common applications is a food product. These systems are usually used when average particle, globule, or bubble, sizes of greater than 20 microns are acceptable in the processed fluid.

Between low energy-high shear mixers and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which may be in the range of from about 0.025 mm to 10.0 mm. Rotors may preferably be driven by an electric motor through a direct drive or belt mechanism. Many colloid mills, with proper adjustment, may achieve average particle, or bubble, sizes of about 0.01 µm to about 25 µm in the processed fluid. These capabilities render colloid mills appropriate for a variety of applications including colloid and oil/water-based emulsion processing such as preparation of cosmetics, mayonnaise, silicone/silver amalgam, and roofing-tar mixtures.

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 are configured to rotate about axis 260, in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances, the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. In embodiments, the inner diameter of the rotor is about 11.8 cm. In embodiments, the outer diameter of the stator is about 15.4 cm. In further embodiments, the rotor and stator may have an outer diameter of about 60 mm for the rotor, and about 64 mm for the stator. Alternatively, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets, or globules, of a fluid that is insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, globules, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, globule or bubble, size less than about 1.5 μm; preferably the globules are sub-micron in diameter. In certain instances, the average globule size is in the range from about 1.0 μm to about 0.1 μm. Alternatively, the average globule size is less than about 400 nm (0.4 μm) and most preferably less than about 100 nm (0.1 μm).

Tip speed is the velocity (n/sec) associated with the end of one or more revolving elements that is transmitting energy to the reactants. Tip speed, for a rotating element, is the circumferential distance traveled by the tip of the rotor per unit of time, and is generally defined by the equation $V$ (m/sec) $= \pi \cdot D \cdot n$, where $V$ is the tip speed, $D$ is the diameter of the rotor, in meters, and $n$ is the rotational speed of the rotor, in revolutions per second. Tip speed is thus a function of the rotor diameter and the rotation rate.

For colloid mills, typical tip speeds are in excess of 23 m/sec (4500 ft/min) and may exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi). The local pressure further depends on the tip speed, fluid viscosity, and the rotor-stator gap during operation.

An approximation of energy input into the fluid (kW/l/min) may be made by measuring the motor energy (kW) and fluid output (l/min). In embodiments, the energy expenditure of a high shear device is greater than 1000 W/m$^3$. In embodiments, the energy expenditure is in the range of from about 3000 W/m$^3$ to about 7500 W/m$^3$. The high shear device 200 combines high tip speeds with a very small shear gap to produce significant shear on the material. The amount of shear is typically dependent on the viscosity of the fluid. The shear rate generated in a high shear device 200 may be greater than 20,000 s$^{-1}$. In embodiments, the shear rate generated is in the range of from 20,000 s$^{-1}$ to 100,000 s$^{-1}$.

The high shear device 200 produces a gas emulsion capable of remaining dispersed at atmospheric pressure for at least about 15 minutes. For the purpose of this disclosure, an emulsion of gas particles, globules or bubbles, in the dispersed phase in product dispersion 210 that are less than 1.5 μm in diameter may comprise a micro-foam. Not to be limited by a specific theory, it is known in emulsion chemistry that submicron particles, globules, or bubbles, dispersed in a liquid undergo movement primarily through Brownian motion effects. The globules in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor. The accelerated rate reactor comprises a single stage, dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, tip speeds, output rpm, and flow rate.

Without wishing to be limited to a particular theory, it is believed that the level or degree of high shear mixing is sufficient to increase rates of mass transfer and may produce localized non-ideal conditions that enable reactions to occur that would not otherwise be expected to occur based on Gibbs free energy predictions. Localized non-ideal conditions are believed to occur within the high shear device resulting in increased temperatures and pressures with the most significant increase believed to be in localized pressures. The increase in pressures and temperatures within the high shear device are instantaneous and localized and quickly revert to bulk or average system conditions once exiting the high shear device. In some cases, the high shear-mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid microcirculation (acoustic streaming). An overview of the application of cavitation phenomenon in chemical/physical processing applications is provided by Gogate et al., "Cavitation: A technology on the horizon," Current Science 91 (No. 1): 35-46 (2006). The high shear-mixing device of certain embodiments of the present system and methods is operated under what are believed to be cavitation conditions effective to dissociate the acetic anhydride into free radicals exposed to crystalline salicylic acid for the formation of the acetyl salicylic acid products.

Description of High Shear Process and System for Production of Aspirin

Figure 2:
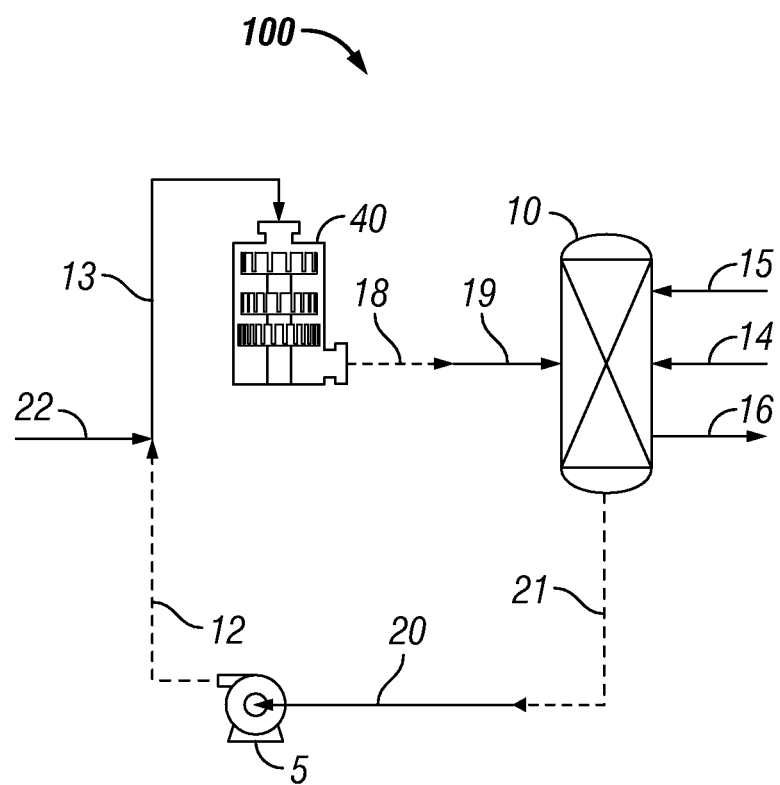
FIG. 2 is a process flow diagram according to an embodiment of the present disclosure for high shear production of aspirin.

High Shear System 100, hereinafter HSS 100, is configured for the conversion of acetic anhydride and salicylic acid to acetyl salicylic acid. FIG. 2 illustrates a flow diagram of an embodiment for the esterification process comprising a high shear device. The disclosed process with the high shear device enhances the conversion by improving contact of reactants. FIG. 2 illustrates the basic components of HSS 100 including pump 5, high shear device (HSD) 40, and reactor 10. In certain embodiments, the HSD 40 is positioned between pump 5 and reactor 10.

Pump 5 is configured to provide a controlled flow throughout high shear system 100. Pump inlet stream 20 comprising acetic anhydride enters pump 5. Pump 5 builds pressure of the pump inlet stream 20 and feeds HSD 40 via pump outlet stream 12. Preferably, all contact parts of pump 5 are stainless steel, for example, type 316 stainless steel. Pump 5 may be any suitable pump, for example, a Roper Type 1 gear pump, Roper Pump Company (Commerce Ga.) or a Dayton Pressure Booster Pump Model 2P372E, Dayton Electric Co (Niles, Ill.).

In certain instances, HSS 100 may combine high shear with increased pressure to enhance reactant mixing. In embodiments, pump 5 increases the pressure of pump inlet stream 20 to greater than about 203 kPa (2 atm). Alternatively, pump 5 increases the pressure to greater than about 2025 kPa (20 atm) prior to pump outlet stream 12. The increased pressure of pump outlet stream 12 can be used to accelerate reactions with the limiting factor being the pressure limitations of pump 5 and high shear device 40.

Pump outlet stream 12 is in fluid communication with HSD inlet stream 13. Pump outlet stream 12 may be continuous with HSD inlet stream 13. In certain embodiments, HSD inlet stream 13 comprises pump outlet stream 12. HSD inlet stream 13 is in fluid communication with the HSD 40.

Dispersible reactant stream 22 is injected into pump outlet stream 12. Dispersible reactant stream 22 is injected into HSD inlet stream 13 comprising pump outlet stream 12 which optionally has undergone further processing, for example heating or cooling. Dispersible reactant stream 22 comprises heated salicylic acid. In further embodiments, dispersible reactant stream 22 comprises crystalline salicylic acid. In certain embodiments, dispersible reactant stream comprises salicylic acid dissolved in suitable solvent. In alternative embodiments, HSD inlet stream 13 and dispersible reactant stream 22 may be injected separately into HSD 40. For example, it can be envisioned that crystalline salicylic acid enters HSD 40 separately from HSD inlet stream 13, comprising pump outlet stream 12.

HSD 40 is in fluid communication with HSD inlet stream 13. HSD 40 intimately mixes the acetic anhydride solution in pump outlet stream 12 with dispersible reactant stream 22 comprising salicylic acid. HSD 40 creates an emulsion of dispersible reactant stream 22 within high shear inlet stream 13. As discussed in detail above, the high shear device 40 is a mechanical device that utilizes, for example, a stator rotor mixing head with a fixed gap between the stator and rotor. HSD 40 combines high tip speeds with a very small shear gap to produce significant shear on the material being processed. The amount of shear will be dependant on the viscosity of the fluid. In high shear device 40, the acetic anhydride and salicylic acid are mixed to form an emulsion comprising microglobules and nano-globules of the salicylic acid dispersed in the acetic anhydride. In certain instances, multiple high shear devices 40 are in fluid communication with HSD inlet stream 13. Further, use of multiple high shear mixers aligned in series, perhaps with varying shear rates, is contemplated to further enhance the reaction.

HSD 40 may form an emulsion of immiscible liquid reactants. Alternatively, HSD 40 increases the dispersion and mixing of miscible liquid reactants in an emulsion. In certain instances HSD 40 a forms a highly mixed liquid-liquid phase (e.g., a fine emulsion) which may also include acetyl salicylic acid product. In embodiments, the resultant emulsion comprises globules in the submicron size. In embodiments, the resultant dispersion has an average globule size less than about 1.5 µm. In embodiments, the mean globule size is less than from about 0.1 µm to about 1.5 µm, preferably the mean globule size is less than about 400 nm; more preferably, less than about 100 nm. In embodiments, the high shear mixing produces globules capable of remaining dispersed at atmospheric pressure for about 15 minutes or longer depending on the globule size.

Without wishing to be limited to a particular theory to explain the mechanical effects of high shear mixing in the high shear process, it is thought that when such emulsion is formed, the surface area available for the reaction between the two phases is significantly increased, leading to an increased rate of reaction. The esterification reaction may initiate once the emulsion has been formed. In this sense, esterification could occur at any point in HSS 100 of FIG. 2 if conditions are suitable. Not to be limited by a specific method, it is known in emulsion chemistry that submicron particles, bubbles, or globules dispersed in a liquid undergo movement primarily through Brownian motion effects.

HSD 40 is in fluid communication with reactor 10. Reactor 10 is any type of reactor in which the esterification reaction of salicylic acid and acetic anhydride can continue. High shear device (HSD) outlet stream 18 comprises an emulsion of micron and/or submicron-sized globules, as discussed hereinabove. HSD outlet stream 18 is fluidly connected to reactor inlet stream 19. HSD outlet stream and reactor inlet stream 19 may be the same stream. In certain instances, the HSD outlet stream 18 may be further processed before entering reactor inlet stream 19. Alternatively, HSD outlet stream 18 may be recycled through the HSD 40 prior to introduction to reactor inlet stream 19. As discussed hereinabove, the esterification may begin in HSD 40, or HSD outlet stream 18 prior to introduction to reactor 10.

In certain embodiments, HSD outlet stream 18 may be heated or cooled prior to introduction to reactor 10. In certain instances, the use of external heat exchangers for heating and/or cooling heat exchangers is within the scope of one of more of the embodiments described and claimed herein. There are many suitable heat transfer devices known to those of skill in the art that may be used successfully without departing from the spirit of the described embodiments. Such exchangers may preferably include, without limitation, shell and tube, plate, and coil heat exchangers, as will be known to those of skill in the art. After processing by heat exchangers, HSD outlet stream 18 is injected into reactor inlet stream 19 for introduction to reactor 10.

Reactor inlet stream 19 is in fluid communication with reactor 10. Reactor inlet stream 19 as introduced to reactor 10 comprises a molar excess of between about 2% and about 20% acetic anhydride compared to salicylic acid. Reactor 10 may preferably be any reactor configured for the esterification of reaction to produce acetyl salicyclic acid. Further, reactor 10 is preferably configured to distill acetyl salicylic acid. Reactor 10 may preferably be a continuous stirred tank reactor or a batch reactor, without limitation. Further, reactor 10 may preferably comprise a jacketed reactor. In certain embodiments, reactor 10 is configured as a holding tank for increased residence time, distillation, and/or agitation of reaction mixture.

Reactor 10 further comprises additional conduits comprising catalyst inlet 14, supplemental reactant inlet 15, product stream 16, and recycle stream 21. In embodiments, the additional conduits are in fluid communication with reactor 10. Catalyst inlet 14 may comprise, for example, catalyst selected from the group consisting of CaO, ZnO, metallic salts, acids, and combinations thereof, as described in U.S. Pat. Nos. 3,373,187 and 6,278,014. In certain embodiments, a reaction mixture may preferably comprise stoichiometric proportions of acetic anhydride and salicylic acid, along with zinc oxide or calcium oxide, which may be introduced via catalyst inlet 14. The resulting reaction is exothermic and produces a mixture of acetyl salicylic acid and calcium acetate or zinc acetate, as described in U.S. Pat. No. 6,278,014. In these embodiments, reactor 10 does not require heating, as the reaction is exothermic and fast.

Supplemental reactant stream 15 may comprise an inert distillable diluent. The diluent is preferably distillable under reaction conditions. For example, the diluent may preferably be selected from the group consisting of acetic acid, benzene, toluene, and xylene. The use of acetic acid as diluent is preferable, as this permits recovery of diluent and byproduct acetic acid in a single step in a relatively pure form. The acetyl salicylic acid recovered in product stream 16 is a dense product that may subsequently be mixed with common excipients, or inactive ingredients, for acetyl salicylic acid, and compressed into tablets immediately after production. Alternatively, a strong acid may preferably be used as a catalyst. For example, concentrated sulfuric acid or phosphoric acid may be used as a catalyst. In embodiments where a strong acid is used as catalyst, disposal of the acid, which may comprise sulfuric acid or phosphoric acid, may be necessary, as will be recognized by the skilled artisan.

Reactor 10 may preferably be configured for maintaining an elevated temperature. Reactor 10 maintains an internal temperature of less than about 98° C., and preferably between about 40° C. to about 95° C. Reactor 10 may be maintained at a reaction temperature for esterification by any method known to those skilled in the art. The elevated temperature may enhance aspirin production when the reaction comprises an excess of acetic anhydride. Alternatively, the elevated temperature may enhance the reaction comprising the addition of acetic acid or other diluents to reactor 10. The use of heat exchangers in thermal communication with reactor 10 is also contemplated within the scope of the contemplated embodiments. By way of illustration and not limitation, further suitable locations for heat exchangers in HSS 100 comprise between the pump 5 and the high shear device 40 and between the high shear device 40 and the reactor 10. Examples of suitable heat exchangers include plate, coil, and shell and tube heat exchangers, as are known to those skilled in the art, without limitation.

In further embodiments, reactor 10 may preferably be configured to apply a vacuum to the reactants. Reactor 10 may comprise a closed vacuum vessel configured to maintain a pressure less than about 4 kPa. Preferably, the reactor 10 is maintained at the minimum obtainable pressure. The low pressure may be maintained for less than about 3 hours. Alternatively, the low pressure is maintained until distillation of the reactants ceases.

In certain embodiments, after complete distillation, the percentage of impurities in the aspirin is reduced by introduction of a quench. Quench may enter reactor 10 by supplemental reactant inlet 15. In certain embodiments, the quench comprises water, acetic acid, or a mixture thereof, without limitation. The quench may be added to reactor 10 following substantial completion of distillation of the reaction mixture, and prior to removal of aspirin crystals. In embodiments, the additional quench comprises from about 1 wt % to about 2 wt % of the reactant concentration in the reactor. The quench may serve to prevent trace amounts of acetic anhydride, or other impurities that remain following distillation, from reacting with the product aspirin crystals. As will be understood by one skilled in the art, impurity reactions with crystalline acetyl salicylic acid may form undesirable, insoluble, sodium carbonate-based compounds.

In HSS 100, acetyl salicylic acid is recovered in a pure dry crystalline form and withdrawn from reactor 10 as product stream 16. In certain embodiments, product stream 16 requires no recrystallization step in the catalyzed embodiments. In embodiments where catalyzed esterification protocols are utilized, no solvent need be removed and/or recycled, and no acids must be removed from the product stream 16.

Alternatively, product stream 16 requires further treatment to recrystallize acetyl salicylic acid and remove acetic acid or acetic anhydride. Excess acetic anhydride, along with any organic diluent recovered as distillate, may be treated and recycled via recycle stream 21. A recycle stream comprising removed organic diluent is returned to the reaction mixture by, for example, recycle stream 21. In further embodiments, recovered acetic acid may be recycled via reactant inlet 15, for introduction and recycling through reactor 10.

The process of the present invention may preferably be conducted under conditions sufficient to promote the esterification of salicylic acid wherein the alcohol group from the salicylic acid reacts with an acid to form an ester acetylsalicylate. It will be understood by those skilled in the art that conditions of temperature and pressure may vary depending on variables such as the reactant concentration, the heating/cooling efficiency of the reactor system, catalyst employed, and other factors without limitation.

In embodiments, use of the disclosed process comprising reactant mixing by HSD 40 provides a faster conversion of acetic anhydride and salicylic acid to aspirin. In certain embodiments, the HSD 40 decreases the quantity of catalysts, reactants, and byproducts, due to more efficient mixing. In embodiments, the method comprises incorporating HSD 40 into an established process, thereby enabling the increase in production (greater throughput) compared to a process operated without HSD 40. Potential benefits of this modified system include, but are not limited to, faster cycle times, increased throughput, reduced operating costs, and/or reduced capital expense due to the possibility of designing smaller reactors and/or operating the reactor at lower residence times. In embodiments, the process of the present disclosure provides for a residence time less than about ¾ the residence time for esterification in the absence of external high shear mixing. Furthermore, the process of the present disclosure provides for a residence time of less than about ½ the residence time (for the same conversion) when compared to esterification in the absence of external high shear mixing.

The method and system of this disclosure enable design of a less capital-intensive process allowing reduced residence times when compared to the residence times previously possible without the incorporation of HSD 40. In embodiments, the disclosed method reduces operating costs/increases production from an existing process. Additionally, the disclosed method may reduce capital costs for the design of new processes.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims that follow, that scope including all equivalents of the subject matter of the claims. The claims are incorporated into the specification as an embodiment of the present invention. Thus, the claims are a further description and are an addition to the preferred embodiments of the present invention. The discussion of a reference in the Description of Related Art is not an admission that it is prior art to the present invention, especially any reference that may have a publication date after the priority date of this application. The disclosures of all patents, patent applications, and publications cited herein are hereby incorporated by reference, to the extent they provide exemplary, procedural, or other details supplementary to those set forth herein.

We claim:

1. A method for producing acetyl salicylic acid, the method comprising:
    forming a dispersion comprising liquid acetic anhydride and liquid salicylic acid utilizing a high shear device, wherein the dispersion comprises salicylic acid globules with a mean diameter of less than about 5 µm, and wherein the high shear device comprises at least one toothed rotor and at least one toothed stator;
    introducing the dispersion into a reactor from which a product comprising acetyl salicylic acid is removed, wherein the operating temperature within the reactor is maintained at a temperature of less than about 98° C.

2. The method of claim 1 further comprising pumping a reactant stream comprising the liquid acetic anhydride to a pressure of at least about 203 kPa to produce a pressurized stream.

3. The method of claim 1 wherein the salicylic acid globules in the dispersion have an average diameter of less than about 1.5 µm.

4. The method of claim 1 wherein forming the dispersion comprises rotating the at least one toothed rotor at a tip speed of at least 5 m/s.

5. The method of claim 1 wherein forming the dispersion comprises rotating the at least one toothed rotor at a tip speed of at least about 20 m/s.

6. The method of claim 4 wherein forming the dispersion comprises producing a localized pressure of about 1000 MPa at the tip of the at least one toothed rotor.

7. The method of claim 1 wherein forming the dispersion comprises subjecting the liquid acetic anhydride and liquid salicylic acid to a shear rate of greater than about 20,000 $s^{-1}$.

8. The method of claim 1 wherein forming the dispersion comprises an energy expenditure of at least 1000 $W/m^3$.

9. The method of claim 1 wherein the dispersion further comprises organic diluent.

10. The method of claim 9 wherein the organic diluent is selected from the group consisting of acetic acid, benzene, toluene, and xylene.

11. The method of claim 1 wherein the dispersion further comprises a catalyst.

12. The method of claim 11 wherein the catalyst is selected from the group consisting of strong acids and metal salts.

13. A method for producing acetyl salicylic acid, the method comprising:
    forming a dispersion of salicylic acid globules in a solution comprising acetic anhydride by introducing liquid salicylic acid and acetic anhydride into a high shear device having at least one toothed rotor/stator pair and subjecting the mixture of liquid salicylic acid and acetic anhydride to a shear rate of at least 20,000 $s^{-1}$.

14. The method of claim 13 wherein the high shear device comprises at least one rotor and at least one stator.

* * * * *